United States Patent [19]

Kiso et al.

[11] Patent Number: 4,673,732

[45] Date of Patent: Jun. 16, 1987

[54] POLYPEPTIDE RELATING TO α-HANP

[75] Inventors: Yoshiaki Kiso, Osaka; Kazuwa Nakao, Kyoto, both of Japan

[73] Assignee: Shionogi & Co., Ltd., Osaka, Japan

[21] Appl. No.: 769,333

[22] Filed: Aug. 26, 1985

[30] Foreign Application Priority Data

Aug. 24, 1984 [JP] Japan ................................. 59-176953

[51] Int. Cl.$^4$ ........................... C07K 7/06; C07K 7/08
[52] U.S. Cl. .................................. 530/326; 530/327; 530/328; 530/329
[58] Field of Search .................. 514/11; 530/326, 327, 530/328, 329

[56] References Cited

U.S. PATENT DOCUMENTS 4,607,023  8/1986  Thibault et al. ..................... 514/11

*Primary Examiner*—Delbert R. Phillips
*Attorney, Agent, or Firm*—Wenderoth, Lind & Ponack

[57] ABSTRACT

The polypeptides represented by the general formula: R-Asn-Ser-Phe-Arg-Tyr-OH wherein R is H, Cys, Gly-Cys, Leu-Gly-Cys, Gly-Leu-Gly-Cys, Ser-Gly-Leu-Gly-Cys, Gln-Ser-Gly-Leu-Gly-Cys, Ala-Gln-Ser-Gly-Leu-Gly-Cys, Gly-Ala-Gln-Ser-Gly-Leu-Gly-Cys, or Ile-Gly-Ala-Gln-Leu-Gly-Cys, and the salt thereof, useful for development of reagents for clinical diagnosis of essential hypertension or in research of pathophysiology.

4 Claims, 1 Drawing Figure

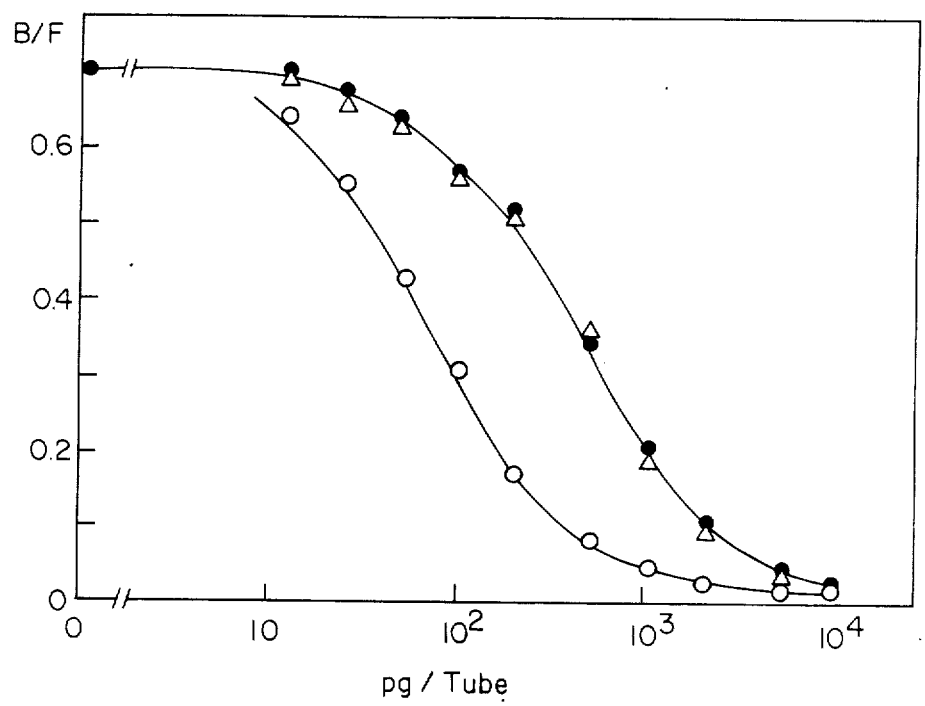

POLYPEPTIDE RELATING TO α-HANP

BACKGROUND OF THE INVENTION

1. Field of the Invention

The present invention relates to polypeptides which are useful for development of a reagent for clinical diagnosis or research in pathophysiology. More particularly, it is concerned with polypeptides useful for etiological diagnosis or pathophysiological investigation for cardiovascular disorders such as essential hypertension.

2. Description of the Prior Art

Recently, Kangawa, Matsuo, et al., have isolated a polypeptide [α-human Atrial Natriuretic Polypeptide=α-hANP] which has a strong natriuretic effect from the human atrium, and identified the structure which is composed of the 28 amino acids as represented by the following structure [Biochem. Biophs. Res. Comm. 118 131 (1984)].

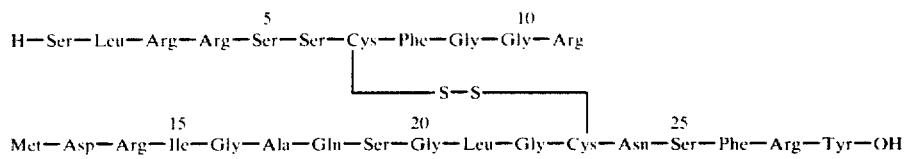

It is reported that the diuretic effect of α-hANP in a biological test using rats is about 1,500 times as potent as that of furosemide which has been used frequently as antihypertensive diuretic. Although some small fragments of the α-hANP [hereinafter sometimes represented by α-hANP-(1-28)], for example, α-hANP-(7-28) [docosapeptide composed of the amino acids of the seventh to twenty eighth from the N-terminal, hereinafter referred in the same manner], α-hANP-(13-28), α-hANP-(18-28) are now commerically available, their physiological effect and their function as an antigen have not yet been reported in any literature. Among these peptides, α-hANP-(18-28) is a pyro-form peptide of which the N-terminal glutamine is cyclized, and the α-hANP-(18-28) of which the N-terminal glutamine is not cyclized is still unknown.

SUMMARY OF THE INVENTION

α-hANP is thought to be one of substances involved in cardiac diseases or essential hypertension. It is an object of the present invention to provide the polypeptides repesented by the general formula: R-Asn-Ser-Phe-Arg-Tyr-OH wherein R is H, Cys, Gly-Cys, Leu-Gly-Cys, Gly-Leu-Gly-Cys, Ser-Gly-Leu-Gly-Cys, Gln-Ser-Gly-Leu-Gly-Cys, Ala-Gln-Ser-Gly-Leu-Gly-Cys, Gly-Ala-Gln-Ser-Gly-Leu-Gly-Cys, or Ile-Gly-Ala-Gln-Ser-Gly-Leu-Gly-Cys, and the salt thereof, useful in preparing antiserum against α-hANP, form which reagents for clinical diagnosis for cardiovascular disorders or used in research of pathophysiology can be developed.

BRIEF DESCRIPTION OF THE DRAWING

FIG. 1 shows the standard curve of α-hANP-(1-28) (represented by ● — ●), the cross curve of α-rANP-(1-28) (represented by Δ—Δ), and α-hANP-(24-28) (represented by ○ — ○), and the vertical axis indicates the ratio of the binding antigen ($^{125}$I marked α-hANP) (B) to the free antigen (F) and the horizontal axis represents the concentration of α-ANP (pg/tube).

DESCRIPTION OF THE PREFERRED EMBODIMENTS

Up to the present, hypertension has been divided into two main classes, that is, primary and secondary hypertension. Secondary hypertension includes mainly those conditions accompanied by renal diseases, endocrine diseases, pregnancy, aortic coarctation, central nervous disorders, and so on. On the other hand, the former, of which the cause is not known, is designated as essential hypertension and 80-90% of the total hypertensives has been classified into this group.

In the case of secondary hypertension, it is possible to improve the condition of hypertension by treatment of causal disease, while in the essential hypertension, the patient has been treated, for example, by antihypertensives, i.e. diuretics vasodilators, and adrenergic inhibitors. Nevertheless, recently it has been suggested that the α-hANP mentioned above is one of substances involved in cardiac diseases or essential hypertension, and the research on the significance of α-hANP in hypertensions has been performed extensively.

The present inventors have continued their research for both elucidating the pathophysiological significance of α-hANP in the control of water and electrolyte balance and establishing a specific method for measurement of α-hANP which is useful to diagnose and evaluate cardiovascular disorders including essential hypertension.

The present invention offers polypeptides for preparing antisera which are indispensable to establish an α-hANP measurement method as mentioned above. More particularly, the present invention relates to the polypeptides represented by the following general formula:

R-Asn-Ser-Phe-Arg-Tyr-OH  (I)

wherein R is
H,
Cys,
Gly-Cys,
Leu-Gly-Cys,
Gly-Leu-Gly-Cys,
Ser-Gly-Leu-Gly-Cys,
Gln-Ser-Gly-Leu-Gly-Cys,
Ala-Gln-Ser-Gly-Leu-Gly-Cys,
Gly-Ala-Gln-Ser-Gly-Leu-Gly-Cys,
or Ile-Gly-Ala-Gln-Ser-Gly-Leu-Gly-Cys,
and the salt thereof.

All of the constituent amino acids in the general formula(I) have the L-form. The abbreviations are described as mentioned below according to the nomenclature of IUPAC (International Union of pure and Applied Chemistry)-IUB (International Union of Biochemistry)

Ala: Alanine
Arg: Arginine

Asn: Asparagine
Cys: Cysteine
Gln: Glutamine
Gly: Glycine
Ile: Isoleucine
Leu: Leucine
Phe: Phenylalanine
Ser: Serine
Tyr: Tyrosine.

The polypeptides represented by the general formula of the present invention and the salts thereof can be manufactured according to the usual synthetic methods elongating the peptide chain, i.e. by condensing amino acids stepwise or coupling the fragments consisting of two to several amino acids, or by a combination of both processes.

The Condensation between two amino acids, or an amino acid and a peptide, or a peptide and a peptide can be carried out according to the usual condensation methods such as the azide method, mixed acid anhydride method, DCC (dicyclohexylcarbodiimide) method, active ester method (p-nitrophenyl ester method, N-hydroxysuccinic acid imido ester method, cyanomethyl ester method, etc.), Woodward reagent κ method, carbonyldiimidazol method, oxidation-reduction method. These condensation reactions may be performed in either liquid phase or solid phase. In the case of elongation the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

As a conventional method for the synthesis of peptides, it is necessary to protect/deprotect the α- and δ-side chain amino groups and the carboxy group of the amino acid as occasion demands. The applicable protective groups to amino groups are exemplified by benzyloxycarbonyl (hereinafter abbreviated as Z), o-chlorobenzyloxycarbonyl [Z(2-Cl)], p-nitrobenzyloxycarbonyl [Z(NO₂)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylphosphinothioyl (Mpt) and the like.

As protective groups for carboxy group there can be exemplified benzyl ester (OBzl), 4-nitrobenzyl ester [OBzl(NO₂)], t-buthyl ester (OBut), 4-pyridylmethyl ester (OPic), and the like. It is desirable that specific amino acids such as arginine, cysteine, and serine possessing a functional group other than amino and carboxyl groups be protected by a suitable protective group as the occasion demands. For example, the guanidino group in arginine may be protected with nitro, p-toluenesulfonyl, benzyloxycarbonyl, adamanthyloxycarbonyl, p-methoxybenzenesulfonyl, 4-methoxy-2,6-dimethylbenzenesulfonyl (Mds), 1,3,5-trimethylphenylsulfonyl (Mts), and the like, the thiol group in cysteine may be protected with benzyl, p-methoxybenzyl, triphenylmethyl, acetylaminomethyl, ethylcarbamoyl, 4-methylbenzyl, 2,4,6-trimethylbenzyl (Tmb) etc, and the hydroxyl group in serine can be protected with benzyl, t-butyl, acetyl, tetrahydropyranyl etc.

An example of preparing α-hANP-(17-28) consisting of 12 amino acids in the present invention is given below in more detail. The reaction sequence can be shown as follows.

The reaction process

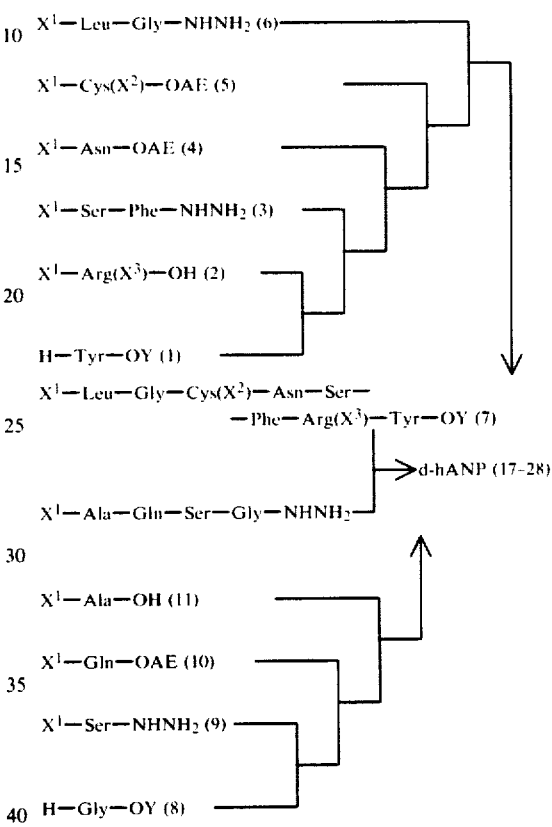

wherein
X¹ represents an amino protective group of N-terminal amino acid,
X² represents a thiol protective group,
X³ represents a guanidyl protective group, AE repersents an active ester residue, and Y represents a carboxy protective group of C-terminal amino acid.

In the above reaction process, the favorable amino-protecting groups for X¹ are Z—, Z(Cl), Z(OMe), Boc and the like, and the favorable carboxyl-protecting groups for Y are —OBzl, OBzl(NO₂) and the like. Tmb is the favorable thiol- protecting group for X² and Mts is the favorable guanidino protecting group for X³.

In the above process, the reaction of (1) with (2), and the introduction of (11) are carried out by means of a mixed acid anhydride method. In the present invention a conventional mixed acid anhydride method utilized for synthesis of peptides is applicable for example, an arginine (2) of which the amino group and guanidino group are protected is allowed to react with ethyl chlorocarbonate or isobutyl chlorocarbonate to give the corresponding anhydride; The reaction for formation of the anhydride is generally carried out under cooling or preferably at −15° to −5° C. for about 10 minutes. The reaction with the anhydride with (1) is carried out in a solvent usually used in syntheses of peptides, for example, dimethylformamide (DMF), dimethylsulfoxide (DMSO), hexamethylphosphoric triamide (HMPA), chloroform, dichloromethane, tetrahydrofuran, dioxane, ethly acetate and the like, under cooling (for example, ice-cooling) for 1-24 hours. The condensation reaction of (11) to (12) is made in the same way. In addition; the hydrazide (12) can be prepared easily from the corresponding ester on reaction with hydrazine hydrate. This hydrazine formation reaction is also utilized in preparation of (3), (6) and (9).

The condensation reaction based on the active ester method, for example, a condensation reaction, of the condensate (1), (2) and (3) with (4), is attained by utilizing as an active ester, p-nitrophenyl ester, 2,4-dinitrophenyl ester, 2,3,4,5,6-pentachlorophenyl ester, 2,4,5-trichlorophenyl ester, 2,3,4,5,6-pentafluorophenyl ester, N-hydroxysuccinate imide ester, or their homologues.

The reaction can generally be carried out under cooling or heating, preferably at a temperature of $-20°$ C.$-40°$ C., in a solvent which can be used for syntheses of peptides as mentioned above. The reaction time is generally 1-24 hours, though it depends on other conditions. These reaction conditions are the same in the condensation reactions of (5) and (10).

The condensation reactions of (3), (6) and (12) are achieved by the azide method. The azide formation from the respective hydrazide is achieved by means of the /Curtius method (Organic Reaction, Vol. 3, p. 337), i.e. reaction with sodium nitrite in an acidic solution or the Rudinger method [Collect. Czech. Chem. Commun., 26, 2333 (1961)] employing alkyl nitrite (for example, isoamylnitrite) in an anhydrous solvent. The reaction of the resulting azide with the corresponding peptide to be condensed is generally carried out at low temperature (from $-10°$ C. to $+10°$ C.) in the presence of a stoichiometric amount of a base. As the base, it is preferable to use organic bases, such as triethylamine, tributylamine, diisopropylethylamine, dimethylaniline, pyridine, picoline, N-methylmorpholine and the like. As the reaction solvent, those which can be used for syntheses of peptides as mentioned above may be properly chosen and used. Before performing the respective above-mentioned reactions, it is necessary to remove the amino protective group represented by $X^1$. For example, a benzyloxycarbonyl-type protecting-group [Z, Z(2Cl), Z(NO$_2$), Z(OMe)] can be removed on treatment with hydrogen fluoride, trifluoroacetic acid, and the like, or by catalytic hydrogenation with palladium.

The protective groups of other functional groups kept until the final step can be removed by a single or stepwise reactions in the final step. For example, Z(OMe) of Ala, Tmb of Cys, Mts of Arg, and Bzl of Tyr can be deprotected by the reaction with hydrogen flouride in the presence of dimethylsulfide, as shown in the following example.

The reaction products in the respective steps and the final products can be isolated and purified by the conventional methods in the peptide field such as extraction, recrystallization, chromatography (gel filtration, ion exchange, partition, adsorption, or reversed phase chromatography), electrophoresis, counter-current distribution.

The peptides shown in the above general formula (I) other than α-hANP-(17-28), can also be manufactured according to the above-mentioned procedure. The salts of the peptides shown by the general formula (I) are exemplified by inorganic or organic acid addition salts such as the hydrochlorides, hydrobromides, nitrates, sulfates, acetates, maleates, formates, lactates, tartrates, succinates and citrates, metal salts such as sodium salts, potassium salts and calcium salts, and ammonium salts or amine salts such as triethylamine salts.

The procedure for the manufacture of the objective compounds of the present invention is given in the following examples. The present invention, however, is not restricted by these examples.

The abbreviation of the protective group used in each following examples has the meaning as shown below.

Z(OMe): p-methoxybenzyloxycarbonyl
ONp: p-nitrophenoxy
Bzl: benzyl
Z: benzyloxycarbonyl
Mts: 1,3,5-trimethylphenylsulfonyl (dimethylene sulfonyl)
Tmb: 2,4,6-trimethylbenzyl.

EXAMPLE 1

Manufacture of α-hANP-(17-28)

(1) Z(OMe)-Arg(Mts)-Tyr-OBzl

A solution of mixed acid anhydride, which is prepared from Z(OMe)-Arg(Mts)-OH [prepared from 10.0 g (16.1 mmol) of the cyclohexylamine salt] and iosbutyl chlorocarbonate in 20 ml of dimethyl formamide (hereinafter abbreviated as DMF), is added to an ice-cooled solution of H-Tyr-OBzl [prepared from 8.25 g (19.3 mmol) of the corresponding toluene sulfonate] in 50 ml of DMF, and the mixture is stirred for 3 hours on an ice bath. The solvent is evaporated under reduced pressure and the oily residue dissolved in ethyl acetate, washed with 0.5N-hydrochloric acid and with an aqueous sodium chloride solution, dried, and evaporated. The residue is crushed and pulverized, chromatographed on a column of silica gel (4.5×25 cm), eluted with a chloroform/methanol (10:0.5) solvent system. The eluate is recrystallized from ethyl acetate/ether to give 11.5 g (92% yield) of the titled compound. mp. 98-102° C. $[\alpha]_D-3.2°$ (c=0.9, DMF, 20° C.), Thin layer chromatography (TLC) [Kiesel gel 60F 245, Merck, hereinafter, the same adsorbent is used]: $Rf_2=0.73$ [the solvent system: chlorofrom/methanol/acetic acid (9:1:0.5), hereinafter, the term $Rf_2$ has the same meaning.]: $Rf_3=0.28$ [the solvent system: chloroform/methanol (10:0.5), hereinafter, the term $Rf_3$ has the same meanings.]

Anal. for $C_{40}H_{47}N_5O_9S_1$: Calcd. (%): C 62.08, H 6.12, N 9.05. Found (%): C 62.19, H 6.16, N 8.66.

(2) Z(OMe)-Ser-Phe-Arg(Mts)-Tyr-OBzl

Trifluoroacetic acid (hereinafter abbreviated as TFA)/anisole (10 ml/2.8 ml) is added to 5.0 g (6.46 mmol) of Z(OMe)-Arg(Mts)-Tyr-OBzl and the mixture treated on an ice bath for 60 minutes, then TFA is evaporated under reduced pressure. The residue is washed with n-hexane, dried on potassium hydroxide (hereinafter abbreviated as KOH) pellets under reduced pressure for 3 hours, and then dissolved in DMF containing 0.9 ml (6.46 mmol) of triethylamine. A solution of an azide prepared from 3.34 g (7.75 mM) of Z(OMe)-Ser-Phe-NHNH$_2$ in DMF [neutralized with 2.59 ml (18.6 mM) of triethlyamine] is added to the above solution under ice-cooling, and the mixture stirred at 5° C. for 14 hours, then concentrated. The residue is purified by the same extraction method as mentioned above, then is chromatographed on a column of silica gel (3.5×20 cm), eluted with a chloroform/methanol (20:0.5) solvent system. The eluate is recrystallized from ethyl acetate/ether to give 4.85 g (76% yield) of the titled compound. mp. 98°–100° C. $[\alpha]_D - 5.1°$ (c=0.6, DMF, 20° C.), TLC: $Rf_1 = 0.67$ [the solvent system: chloroform/methanol/water (8:3:1), hereinafter, the term $Rf_1$ has the same meaning.]

Anal. for $C_{52}H_{61}N_7O_{12}S$: Calcd. (%): C 61.95, H 6.10, N 9.37. Found (%): C 62.03, H 6.08, N 9.67.

(3) Z(OMe)-Asn-Ser-Phe-Arg(Mts)-Tyr-OBzl

Protected tetrapeptide ester (4.50 g; 4.46 mmol) obtained in the above procedure (2) is treated with TFA/anisole (10 ml/2.4 ml) in the same manner as mentioned above, and then dry ether added thereto. The resulting precipitate is washed with ether, dried on KOH pellets under reduced pressure for 3 hours, and then dissolved in 20 ml of DMF. To this solution are added 0.62 ml (4.46 mmol) of triethylamine, 2.05 g (4.91 mmol) of Z(OMe)-Asn-ONp, and 0.49 ml (4.46 mmol) of N-methylmorpholine (hereinafter, abbreviated as NMM), then the mixture is stirred for 14 hours, neutralized with acetic acid, and evaporated. The residue is crushed and pulverized in ether/water. The powder is precipitated from DMF with addition of ethanol to give 3.95 g (79% yield) of the titled compound.

mp. 171°–173° C. $[\alpha]_D - 15.0°$ (c=0.6, DMF, 20° C.), TLC: $Rf_1 = 0.63$.

Anal. for $C_{56}H_{67}N_9O_{14}S$: Calcd. (%): C 59.93, H 6.02, N 11.23. Found (%): C 59.79, H 6.08, N 11.14.

(4) Z(OMe)-Cys(Tmb)-OH

Under ice-cooling, a solution of 4.91 g (23.7 mmol) of $Z(OMe)-N_3$ in 25 ml of tetrahydrofuran (hereinafter, abbreviated as THF) is added to a solution of 5.0 g (19.7 mM) of H-Cys(Tmb)-OH in 25 ml of water containing 6.0 ml (43.3 mmol) of triethylamine. After stirring at 5° C. overnight, the reaction mixture is washed with ether, and then the aqueous layer is neutralized with 5% citric acid. The resulting precipitate is dried to give powder, which is recrystallized from DMF/ether to give 4.59 g (56% yield) of the titled compound. mp. 153°–158° C. $[\alpha]_D - 37.5°$ (c=0.6, DMF, 20° C.) TLC: $Rf_1 = 0.56$.

Anal. for $C_{22}H_{27}NO_5S$: Calcd. (%): C 63.29, H 6.52, N 3.36. Found (%): C 63.49, H 6.54, N 3.41.

(5) Z(OMe)-Cys(Tmb)-ONp

To a solution of 5.0 g (12.0 mM) of Z(OMe)-Cys(Tmb)-OH and 1.83 g (13.2 mmol) of p-nitrophenol in 50 ml of THF is added 2.72 g (13.2 mmol) of dicyclohexylcarbodiimide (hereinafter abbreviated as DCC). After stirring at room temperature overnight, the mixture is filtered. The filtrate is concentrated and the product is purified by crystallization from DMF/2-propanol to give 3.56 g (55% yield) of the titled compound. mp. 121° C. $[\alpha]_D - 25.5°$ (c=1.0, DMF, 20° C.), TLC: $Rf_5 = 0.71$ [the solvent system: chloroform, hereinafter, the term $Rf_5$ has the same meaning.], Anal. for $C_{28}H_{30}N_2O_7S$: Calcd. (%): C 62.44, H 5.61, N 5.20. Found (%): C 62.40, H 5.61, N 5.20.

(6) Z(OMe)-Csy(Tmb)-Asn-Ser-Phe-Arg(Mts)-Tyr-OBzl

With TFA/anisole (4 ml/1 ml) is treated 2.0 g (1.78 mmol) of Z(OMe)-Asn-Ser-Phe-Arg(Mts)-Tyr-OBzl in a usual way, then dry ether is added to the mixture to give the powdery product. After being dried on KOH pellets under reduced pressure for 3 hours, the powder is dissolved together with 0.23 ml (1.78 mmol) of triethylamine, 1.06 g (1.96 mmol) of Z(OMe)-Cys(Tmb)-ONp, and 0.20 ml (1.78 mM) of NNM in 20 ml of DMF. The solution is stirred for 14 hours, neutralized with acetic acid, and evaporated. The residue is crushed in water, and the obtained powder is precipitated from DMF-ethanol to give 2.01 g (83% yield) of the titled compound. mp. 200°–203° C. $[\alpha]_D - 200°$ (c=0.8, DMF, 20° C.) TLC: $Rf_1 = 0.51$.

Anal. For $C_{69}H_{84}N_{10}O_{15}S_2$: Calcd. (%): C 61.04, H 6.24, N 10.32. Found (%): C 60.85, H 6.40, N 10.03.

(7) Z(OMe)-Leu-Gly-NHNH$_2$

To the solution of 7.02 g (19.7 mmol) of Z(OMe)-Leu-Gly-OMe in 30 ml of methanol is added 5.90 ml (98.5 mmol) of 80% hydrazine hydrate. The mixture is allowed to react at room tempreature for 24 hours, and evaporated. Water/ether is added to the residue to crystallize. The crystals are recrystallized from methanol/ether to give 5.97 g (83% yield) of the titled compound. mp. 108°–112° C. $[\alpha]_D - 6.0°$ (c=0.7, DMF, 20° C.).

Anal. for $C_{17}H_{26}N_4O_5$: Calcd. (%): C 55.72, H 7.15, N 15.29. Found (%): C 55.74, H 7.15, N 15.20.

(8) Z(OMe)-Leu-Gly-Cys(Tmb)-Asn-Ser-Phe-Arg(Mts)-Tyr-Obzl

TFA/aninole (4.0 ml/1.0 ml) is added to 2.01 g (1.48 mmol) of Z(OMe)-Cys(Tmb)-Asn-Ser-Phe-Arg(Mts)-Tyr-OBzl and the mixture is allowed to react in the usual manner at 0° C. for 1 hours. TFA is evaporated, and the residue is crushed and pulverized in ether. The powder is collected by filtration, and dried to give H-Cys(Tmb)-Asn-Ser-Phe-Arg(Mts)-Tyr-OBzl.TFA. The powder is dissolved in DMF containing 0.21 ml of triethylamine. An azide solution (neutralized with 0.59 ml of triethylamine) which is prepared from 0.65 g (1.78 mmol) of Z(OMe)-Leu-Gly-NHNH$_2$ on treatment with 0.28 ml (2.14 mmol) of isoamylnitrite/3.2M-HCl/DMF (0.28 ml/1.34 ml) in DMF is added to the above solution under ice-cooling. The mixture is stirred at 5° C. for 14 hours. The reaction mixture is concentrated and water is added to the residue. The product is crystallized from DMF/ethanol to give 2.06 g (91% yield) of the titled compound. mp. 210°–212° C. $[\alpha]_D - 11.4°$ (c=0.7, DMF, 20° C.), TLC: $Rf_1 = 0.56$.

Anal. for $C_{77}H_{98}N_{12}O_{17}S_2$: Calcd. (%): C 60.53, H 6.47, N 11.00. Found (%): C 60.29, H 6.69, N 10.85.

(9) Z(OMe)-Ser-Gly-OBzl

To an azide solution (neutralized with 8.26 ml of triethylamine) which is prepared from 7.0 g (24.7 mmol) of Z(OMe)-Ser-NHNH$_2$ is allowed to react in the usual way with 3.94 ml of isoamylnitrite/18.6 ml of 3.2N-HCl-DMF in 10 ml of DMF is added 9.51 g (29.6 mmol) of H-Gly-OBzl.toluenesulfonate in 30 ml of DMF solution (neutralized with 4.11 ml of triethylamine) under ice-cooling, and the mixture is allowed to react at 5° C. for 14 hours. The reaction mixture is concentrated, and the oily residue is dissolved in ethyl acetate. The solution is washed with 0.5N hydrochloric acid, 5% sodium hydrogen carbonate, and saturated sodium chloride aqueous solution, dried over sodium sulfate, and evaporated. Ether is added to the residue to crystallize. The crystals are recrystallized from THF/ether to give 6.89 g (67% yield) of the titled compound. mp. 95°–97° C. $[\alpha]_D + 3.0°$ (c=0.7, DMF, 20° C.), TLC: $Rf_1 + 0.89$, $Rf_3 = 0.33$.

Anal. for $C_{21}H_{24}N_2O_7$: Calcd. (%): C 60.57, H 5.81, N 6.73. Found (%): C 60.67, H 5.78, N 6.84.

(10) Z(OMe)-Gln-Ser-Gly-OBzl

With TFA/anisole (10 ml/2.6 ml) is treated 5.0 g (12.0 mmol) of Z(OMe)-Ser-Gly-OBzl to remove the protecting group. The product is dissolved in 20 ml of DMF, the solution is neutralized with 3.34 ml (24.0 mmol) of triethlyamine, then 5.69 g (13.2 mmol) of Z(OMe)-Gln-ONp is added to the solution, and the mixture stirred for 14 hours. The solution is concentrated, the resulting solid residue is washed with 10% citric acid and water, and recrystallized from DMF/methanol to give 5.04 g (77% yield) of the titled compound. mp. 198°–200° C. $[\alpha]_D + 3.9°$ (c=0.5, DMF, 20° C.), TLC: $Rf_1 = 0.12$.

Anal. for $C_{26}H_{32}N_4O_9$: Calcd. (%): C 57.34, H 5.92, N 10.29. Found (%): C 57.31, H 5.98, N 10.43

(11) Z(OMe)-Ala-Gln-Ser-Gly-Obzl

With TFA/anisole (6.0 ml/1.8 ml) is treated 3.0 g (5.51 mmol) of the tripeptide obtained in the above procedure (10) in the usual way to deprotect. The product is dissolved in 30 ml of DMF containing 0.77 ml (5.51 mmol) of triethylamine. Under ice-cooling, a solution of mixed acid anhydride (DMF 20 ml) which is prepared from 1.67 g (6.61 mmol) of Z(OMe)-Ala-OH and 0.945 ml (7.27 mmol) of isobutylchlorocarbonate is added to the above solution. The mixture is stirred on an ice bath for 3 hours. The solvent is evaporated, the solid product which is deposited from the residue with addition of water is collected by filtration, and recrystallized from DMF/ethanol to give 2.72 g (80% yield) of the titled compound. mp. 105°–107° C. $[\alpha]_D - 3.6°$ (c=0.8, DMF, 20° C.), TLC: $Rf_1 = 0.62$.

Anal. for $C_{29}H_{37}N_5O_{10}$: Calcd. (%): C 56.57, H 6.06, N 11.38. Found (%): C 56.71, H 6.10, N 11.58.

(12) Z(OMe)-Ala-Gln-Ser-Gly-NHNH$_2$

In 30 ml of DMF solution is dissolved 2.72 g (4.42 mmol) of the protected tetrapeptide ester perpared in the above precedure (11), 1.3 ml (5 equivalent) of 80% hydrazine hydrate is added thereto, and the mixture is allowed to react for 24 hours. The solvent is evaporated. The powdery residue is washed with ethanol, and then recrystallized from dimethyl sulfoxide (hereinafter, abbreviated to as DMSO)-DMF (1:1)/ethanol give 2.29 g (96% yield) of the titled compound. mp. 216°–218° C. $[\alpha]_D - 19.1°$ (c=0.7, DMSO, 20° C.), TLC: $Rf_1 = 0.21$.

Constituting amino acids (%) of the hydrolysate with 6N-HCl: Ser. 0.90, Glu 1.02, Gly 1.00, Ala 1.02. (recovery of Gly 89%).

Anal. for $C_{22}H_{33}N_7O_9$: Calcd. (%): C 48.97, H 6.17, N 18.17. Found (%): C 48.67, H 6.38, N 18.17.

(13) Z(OMe)-Ala-Gln-Ser-Gly-Leu-Gly-Cys(Tmb)-Asn-Ser-Phe-Arg(Mts)-Tyr-OBzl [Z(OMe)-(hANP 17-28)-OBzl]

With TFA/anisole (4 ml/1 ml) is made 2.06 g (1.35 mmol) of Z(OMe)-Leu-Gly-Cys(Tmb)-Asn-Ser-Phe-Arg(Mts)-Tyr-OBzl to react at 0° C. for 60 minutes. After TFA is evaporated at room temparature, dry ethanol is added to the residue to give the powdery precipiate of H-Leu-Gly-Cys(Tmb)-Asn-Ser-Phe-Arg(Mts)-Tyr-OBzl.TFA. The product is collected by filtration, dried on the KOH pellets for 3 hours under reduced pressure, and then dissolved in 10 ml of DMF containing 0.19 ml (1.35 mmol) of triethlyamine.

On the other hand, 1.09 g (2.03 mmol) of Z(OMe)-Ala-Gln-Ser-Gly-NHNH$_2$ is dissolved in 10 ml of DMF-DMSO (1:1), and 1.22 ml (4.87 mmol) of 4.0N-hydrochloric acid/DMF and 0.32 ml (2.44 mmol) of isoamylnitrile are successively added to the solution. The mixture is allowed to react under cooling, and neutralized with 0.68 ml (4.87 mmol) of triethylamine to give the corresponding azide. This azide solution is dropwise added to the above solution of octapeptide in DMF under ice-cooling, and the mixture is stirred at 5° C. overnight. After the confirmation of negative ninhydrin reaction, the reaction mixture is diluted with 50 ml of water. The resulting powdery precipitate is collected by filtlation, dried, and recrystallized from DMF/90% methanol to give 2.37 g (94% yield) of the titled compound.

mp. 242°–244° C., $[\alpha]_D - 7.1°$ (c=0.6, DMSO, 20° C.), TLC: $Rf_4 = 0.85$ [the solvent system: n-butanol/pyridine/acetic acid/water (4:1:1:2)].

Constituting amino acids (%) of the hydrolysate with 6N-HCl: Asp 1.03, Ser 1.90, Glu 1.21, Gly 2.17, Ala 1.17, Cys 0.66, Leu 0.98, Tyr 0.97, Phe 1.00, Arg 1.03. (recovery of Phe 97%).

Anal. for $C_{90}H_{119}N_{17}O_{23}S_2$: Calcd. (%): C 57.77, H 6.41, N 12.73. Found (%): C 57.56, H 6.48, N 12.51.

(14) H-Ala-Gln-Ser-Gly-Leu-Gly-Cys(SH)-Asn-Ser-Phe-Arg-Tyr-OH [α-hANP-(17-28)]

To 100 mg (53.4 μmol) of Z(OMe)-[α-hANP-(17-28)]-OBzl obtained in the above procedure (13) are added 280 μl(2.67 μmol) of m-cresol, 196 μl (2.67 μmol) of dimethyl sulfide, and 2 ml of hydrogen fluoride, the mixture is treated at 0° C. for 1 hour, and hydrogen fluoride is evaporated at 0° C. Ether is added to the residue, and the resulting powdery substance is centrifuged, dissolved in 2 ml of water containing 82 mg (10 equivalent) of dithiothreitol, and adjusted to pH 8 with addition of 3% aqueous ammonia. The mixture is stirred for 30 minutes under flowing argon. The reaction mixture is purified through Sephadex G-25 (Pharmacia AB) (1.8×140 cm, eluted with 0.2N acetic acid: The volume of each fraction is 7 ml.). The eluate is freeze-dried to give 23 mg (33% yield) of the titled compound.

$[\alpha]_D - 10.0°$ (c=0.1, 0.2N acetic acid, 30° C.), TLC: $Rf_4 = 0.37$ Constituting amino acids (%) of the hydrolysate with 6N-HCl: Asp 0.98, Ser 1.85, Glu 1.03, Gly 2.02, Ala 1.09, CySH 1.36, Leu 0.99, Tyr 0.78, Phe 1.00, Arg 0.97. (recovery of Phe 92%).

EXAMPLE 2

Manufacture of α-hANP-(24–28)

To 93 mg (0.0829 mmol) of Z(OMe)-Asn-Ser-Phe-Arg(Mts)-Tyr-OBzl, the protected pentapeptide obtained in the above procedure in Example 1-(3), are added 87 μl (0.829 mmol) of m-cresol, 59 μl (0.829 mmol) of dimethyl sulfide, and 2 ml of hydrogen fluoride. After the mixture is allowed to react at 0° C. for 1 hour, hydrogen fluoride is evaporated at 0° C., and the residue is worked up in the same manner as (14) in Example 1 to give 34 mg of α-hANP-(24–28) [H-Asn-Ser-Phe-Arg-Tyr-OH].

EXAMPLE 3

Manufacture of H-Ile-Gly-Ala-Gln-Ser-Gly-Leu-Gly-Cys(SH)-Asn-Ser-Phe-Arg-Tyr-OH [α-hANP-(15–28)]

With 0.23 ml (2.14 mmol) of anisole and 2 ml of trifluoroacetic acid is allowed 500 mg (0.267 mmol) of Z(OMe)-Ala-Gln-Ser-Gly-Leu-Gly-Cys(Tmb)-Asn-Ser-Phe-Arg(Mts)-Tyr-OBzl to react at 0° C. for 1 hour. Trifluoroacetic acid is evaporated at room temperature, ether is added to the residue to pulverized, and the powder is collected by filtration and dried to give the deprotected product as the trifluoroacetate from which Z(OMe) has been removed, i.e. H-Ala-Gln-Ser-Gly-Leu-Gly-Cys(Tmb)-Asn-Ser-Phe-Arg(Mts)-Tyr-OBzl.TFA.

Separately, 127 mg of Z(OMe)-Ile-Gly-NHNH₂ is made to react with 5 ml of DMF, 208 μl of 4.0N-HCl/DMF, 55 μl of isoamylnitrite, and 116 μl of triethlyamine to give the corresponding azide. The azide is dropwise added to the above deprotected product in DMSO-DMF (1:1) under ice-cooling, and the mixture is allowed to stand overnight under stirring. The solid matter which is produced from the reaction mixture with addition of water is collected by filtration, dried, and further purified by reprecipitation from DMF/methanol to give 433 mg (79.4% yield) of the desired protected α-hANP-(15-28), that is, Z(OMe)-Ile-Gly-Ala-Gln-Ser-Gly-Leu-Gly-Cys(Tmb)-Asn-Ser-Phe-Arg(Mts)-Tyr-OBzl. TLC: Rf₁=0.47.

Constituting amino acids (%) of the hydrolysate with 6N-HCl: Asp 1.00(1), Ser 1.83(2), Gln 1.21(1), Cystein 0.60(1), Gly 3.46(3), Ala 1.24(1), Ile 1.07(1), Leu 1.20(1), Tyr 0.92(1), Phe 1.00(1), Arg 0.92(1). (recovery of Phe 63%).

The above protected α-hANP-(15-28) (100 mg; 0.049 mmol) is treated with 180 μl (2.45 mmol) of methyl sulfide and 2 ml of hydrogen fluoride in 257 μl (2.47 mmol) of m-cresol at 0° C. for 1 hour. Hydrogen fluoride is evaporated under reduced pressure at 0° C. The residue is pulverized with addition of ether. The powder is collected by centrifugation. The product is dissolved in 2 ml of aqueous solution containing 75 mg of dithiothreitol. The mixture is adjusted to pH 8 with addition of 5% aqueous ammonia, and stirred under flowing argon for 30 minutes. The reaction product is chromatographed on a column of Sephadex G-25 (1.8×110 cm) (Parmacia AB), and eluted with 0.2N acetic acid (The volume of each fraction, 6 ml). The fractions 30 to 37 are freeze-dried to give 58 mg of the titled compound, α-hANP-(15-28), in 80% yield. TLC: Rf₄=0.29.

It has been confirmed as shown in the following experiment the polypeptide α-hANP-(n-28) (n stands for an integer of 15 to 24) obtained by means of the present invention has an antigenicity against animal as α-hANP-(1-28) has and that these polypeptides can be utilized in a radioimmunoassay specific to α-hANP in order to elucidate a pathophysiological role in a capacity-controlling system of α-hANP.

EXPERIMENT 1

Combination of α-hANP-(17-28) with bovine tyroglobulin (Preparation of the complex)

α-hANP-(17-28) is combinded with bovine tyroglobulin by the carbodiimido-coupling method [Yoshimasa et al., J. Clin. Invest. 69, 643 (1983), Nakao et al., Biochem. Biophys. Res. Commun. 117, 695 (1984)]

In 2 ml of distilled water were dissolved 3 mg of α-hANP-(17-28) and 25.2 mg of bovine tyroglobulin, and a solution of 30 mg of 1-ethyl-3-(3-dimethylaminopropyl)carbodiimide hydrochloride was added thereto. The mixture was adjusted to pH 5.6 with addition of hydrochloric acid, and stirred at room temperature for 20 hours. The reaction mixture was dialyzed 3 times at 4° C. for 5 l of distilled water to give the complex.

Immunization

In an equal volume of Freund's complete adjuvant was suspended 100-200 μg of α-hANP-(17-28)-tyroglobulin complex.

Japanese white rabbits were immunized with the suspension by subcutaneous injection to their interscapular vertebrae area. Every 4 weeks, the booster was done to them, and 10-14 days after the each booster, the blood was collected from them to give antiserum CR₃.

Iodination

Iodination was made on 1 μg of α-hANP-(1-28) with 1 mCi ¹²⁵I₂ in a usual manner according to the chloramin T method [Nature, 194 495 (1962)]. The reaction mixture was passed through a Sep-Pak cartridge (Waters Ltd.) and eluted with a 50% acetonitril/5 mM trifluoroacetic acid mixture to give the pure product. The specific activity of the ¹²⁵I-labelled α-hANP was 700 μCi/μg.

Radioimmunoassay (RIA)

As a buffer solution for RIA, 0.1M phosphate buffer containing 0.5% gelatin, 0.1 mM EDTA-2Na, 0.2 mM cystine, 0.1% Triton X-100 and 0.01% merthiolate was used.

To 100 μl of a standard solution of α-hANP were added 100 μl of antiserum CR₃ solution (4000-fold final dilution), 100 μl of ¹²⁵I-α-hANP (about 5,000 cpm), and 200 μl of the buffer for RIA, and the mixture was incubated at 4° C. for 72 hours.

A dextran-coated charcoal suspension (1 ml) consisting of 300 mg/100 ml of charcoal (Norit SX Plus), 30 mg/100 ml of dextran (Dextran T-70, Pharmacia AB), and 1 ml of 0.05M phosphate buffer containing 0.01% merthiolate was added thereto. The mixture was allowed to stand at 4° C. for 15 minutes, then the conjugate of ¹²⁵I labelled α-hANP was separated by centrifugation from the free form, and the radioactivity was measured.

Conclusion

The standard curve of α-hANP-(1-28) and the cross curve of α-rANP-(1-28) isolated from the rat atrium and of the synthetic peptide fragment α-hANP-(24-28) are shown in FIG. 1. The minimum detection limit was 50 pg high in sensitivity. As it is clear from FIG. 1, the antiserum CR₃ prepared from α-hANP-(17-28) recognizes α-hANP-(1-28) equally; on the other hand, it is confirmed from the molecular weight conversion that α-hANP-(24-28) also shows the equivalent activity to that of α-hANP-(1-28). The RIA could detect α-ANP-LI in extracts from dog, guinea pig, monkey, bovine, porcine, and sheep atria as expected. The result indicates that RIA system as mentioned above is applicable not only for detection of α-hANP but also for α-ANP related peptides from other animal species. The system is also applicable to detection of other natural or synthetic α-ANP like peptides of which the amino acid sequence has not yet been determined.

What is claimed is:

1. A polypeptide represented by the general formula:

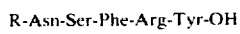

R-Asn-Ser-Phe-Arg-Tyr-OH wherein R is
H,
Cys,
Gly-Cys,
Leu-Gly-Cys,
Gly-Leu-Gly-Cys,
Ser-Gly-Leu-Gly-Cys,
Gln-Ser-Gly-Leu-Gly-Cys,
Ala-Gln-Ser-Gly-Leu-Gly-Cys, Gly-Ala-Gln-Ser-Gly-Leu-Gly-Cys,
or Ile-Gly-Ala-Gln-Ser-Gly-Leu-Gly-Cys,
and the salt thereof.

2. The polypeptide claimed in claim 1, wherein R is hydrogen or its salt.

3. The polypeptide claimed in claim 1, wherein R is Ala-Gln-Ser-Gly-Leu-Gly-Cys, or its salt.

4. The polypeptide claimed in claim 1, wherein R is Ile-Gly-Ala-Gln-Ser-Gly-Leu-Gly-Cys, or its salt.

* * * * *